United States Patent

Drabek

[11] 4,000,314
[45] Dec. 28, 1976

[54] PESTICIDAL N-(2,2-DICYANOVINYL)-N-BENZYL-ANILINES

[75] Inventor: Jozef Drabek, Allschwil, Switzerland

[73] Assignee: Ciba-Geigy Corporation, Ardsley, N.Y.

[22] Filed: Jan. 6, 1976

[21] Appl. No.: 646,815

[30] Foreign Application Priority Data

Jan. 16, 1975 Switzerland ............ 533/75
Oct. 22, 1975 Switzerland ............ 13666/75

[52] U.S. Cl. ............ 424/304; 260/465 E
[51] Int. Cl.$^2$ ............ A01N 9/20; C07C 121/78
[58] Field of Search ............ 260/465 E; 424/304

[56] References Cited

UNITED STATES PATENTS 3,551,573  12/1970  Baker et al. ............ 424/304

Primary Examiner—Lewis Gotts
Assistant Examiner—Dolph H. Torrence
Attorney, Agent, or Firm—Frederick H. Rabin

[57] ABSTRACT

Compounds of the formula

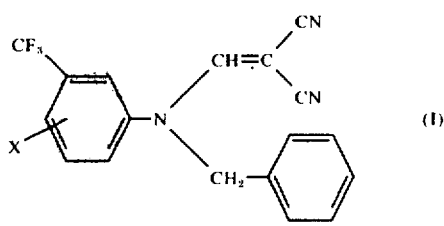

wherein X represents a chlorine atom or trifluoromethyl group in the 4- or 5-position exhibit valuable pesticidal, in particular acaricidal and insecticidal, properties.

7 Claims, No Drawings

PESTICIDAL N-(2,2-DICYANOVINYL)-N-BENZYL-ANILINES

The present invention relates to new N-(2,2-dicyanovinyl)-N-benzyl-anilines which have a pesticidal action, to processes for producing them, as well as to pestcontrol agents containing these anilines as active ingredients, and to processes for combatting pests by application of the new compounds.

The invention relates in particular to compounds of the formula I

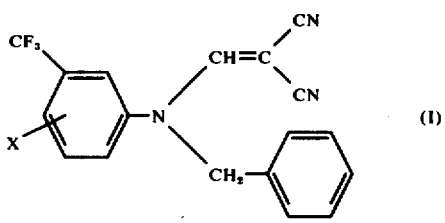

wherein
X stands for a chlorine atom or a trifluoromethyl radical in the 4- or 5-position.

The new compounds of the formula I are obtained by methods known per se; for example by reaction of a compound of the formula II

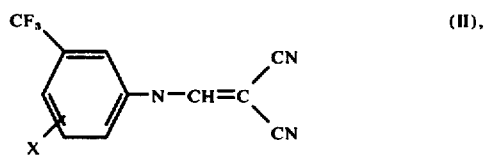

wherein X has the meaning already given under formula I, with a benzyl halide of the formula III

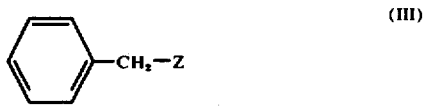

wherein Z stands for a halogen atom, especially for a chlorine or bromine atom, in the presence of an acid-binding agent.

Suitable acid-binding agents are, in particular, tertiary amines such as trialkylamines and pyridine, also hydroxides, oxides, carbonates and bicarbonates of alkali metals and alkaline-earth metals, as well as alkali metal alcoholates such as potassium-t.-butylates and sodium methylate.

The reaction is performed preferably under normal pressure at a temperature of between 0° and 120° C, usually between 20° and 100° C, and in the presence of a solvent or diluent inert to the reactants. Suitable solvents or diluents are, for example, aromatic hydrocarbons, especially chlorobenzene, polychlorobenzenes and bromobenzene; chlorinated alkanes having 1 to 3 carbon atoms; ethers such as dioxane and tetrahydrofuran; esters such as ethyl acetate; ketones such as acetone, methyl ethyl ketone and diethyl ketone; formamide; nitriles such as acetonitrile; alcohols such as ethyl alcohol; dimethylsulphoxide and water.

The starting materials of the formula II are known and can be produced by known methods (see U.S. Pat. No. 3,551,573).

The compounds of the formula I are suitable for combatting various animal and plant pests. They are particularly suitable for combatting insects of the families: Acrididae, Blattidae, Gryllidae, Gryllotalpidae, Tettigoniidae, Cimicidae, Pyrrhocoridae, Reduviidae, Aphididae, Delphacidae, Diaspididae, Pyseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae.

In particular, however, the compounds of the formula I are suitable for combatting insects which do damage to plants, especially insects which do damage to plants by eating, in ornamental crops and in useful crops, such as in cotton and rice crops.

This insecticidal action can be substantially broadened and adapted to suit given circumstances by the addition of other insecticides. Suitable additives are, e.g.: organic phosphorus compounds, nitrophenols and derivatives thereof, formamidines, ureas, pyrethrin-like derivatives, carbamates or chlorinated hydrocarbons.

Also to be noted is the favourable toxicity of the compounds of the invention towards warm-blooded animals, e.g. compared with that of the analogues known from the U.S. Pat. No. 3,551,573.

The compounds of the formula I can be used on their own or together with suitable carriers and/or additives. Suitable carriers and additives can be solid or liquid and they correspond to the substances common in formulation practice, such as natural or regenerated substances, solvents, dispersing agents, wetting agents, adhesives, thickeners, binders and/or fertilizers.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations:

dusts, scattering agents, granulates (coated granulates, impregnated granulates and homogeneous granulates);

liquid preparations:

a. water-dispersible active-substance concentrates: wettable powders, pastes or emulsions;
b. solutions.

The content of active substance in the described compositions is between 0.1 and 95%; in this connection it is to be mentioned that in the case of application from an aeroplane, or by means of other suitable devices, a concentration of up to 99.5% can be employed, or even the pure active substance.

The active substances of the formula I can be formulated, for example, as follows (parts denote parts by weight):

Dusts:

The following substances are used in the preparation of (a) a 5% dust, and (b) a 2% dust:
a.
5 parts of active substance, 95 parts of talcum;

b.
2 parts of active substance,
1 part of highly dispersed silicic acid,
97 parts of talcum.

The active substances are mixed and ground with the carriers.

Granulate:

The following substances are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder:

The following constituents are used to prepare (a) a 40%, (b) and (c) a 25%, and (d) a 10% wettable powder:

a.
40 parts of active substance,
5 parts of sodium lignin sulphonate,
1 part of sodium dibutyl-naphthalene sulphonate,
54 parts of silicic acid;

b.
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

c.
25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminum silicate,
16.5 parts of kieselguhr,
46 parts of kaolin;

d.
10 parts of active substance,
3 parts of a mixture of the sodium salts of saturated fatty alcohol sulphates,
5 parts of naphthalenesulphonic acid/ formaldehyde condensate,
82 parts of kaolin.

The active substances are intimately mixed in suitable mixers with the additives, and the mixture is then ground in the appropriate mills and rollers. Wettable powders are obtained which can be diluted with water to give suspensions of any desired concentration.

Emulsifiable concentrates:

The following substances are used to produce (a) a 10%, (b) a 25%, and (c) a 50% emulsifiable concentrate:

a)
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

b.
25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;

c.
50 parts of active substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of any desired concentration. Spray:

The following constituents are used to prepare (a) a 5% spray, and (b) a 95% spray:

a.
5 parts of active substance,
1 part or epichlorohydrin,
94 parts of ligroin (boiling limits 160°–190° C);

b.
95 parts of active substance,
5 parts of epichlorohydrin.

The invention is further illustrated by the following Examples.

EXAMPLE 1

Production of N-(2,2-dicyanovinyl)-N-benzyl-3,5-bistrifluoromethylaniline 30.4 g of N-(2,2-dicyanovinyl)-aniline is dissolved in a solution of 5.61 g of KOH in 100 ml of methanol. The methyl alcohol is distilled off and the residue is suspended in 150 ml of acetonitrile. To this suspension there is added 12.6 g of benzyl chloride and the reaction mixture obtained is stirred for three hours at 60°–70° C. The mixture is afterwards cooled; it is filtered with suction and the acetonitrile is distilled off. The crude product is suspended in hot carbon tetrachloride and is then filtered off hot under suction. After cooling, there crystallises from the filtrate N-(2,2-dicyanovinyl)-N-benzyl-3,5-bistrifluoromethyl-aniline of the formula

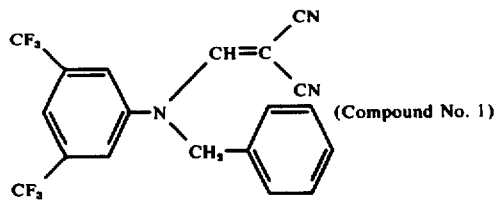

(Compound No. 1)

in the form of yellow crystals having a melting point of 93° to 96° C.

The following compound is produced in an analogous manner. N-(2,2-dicyanovinyl)-N-benzyl-3-trifluoromethyl-4-chloroaniline of the formula

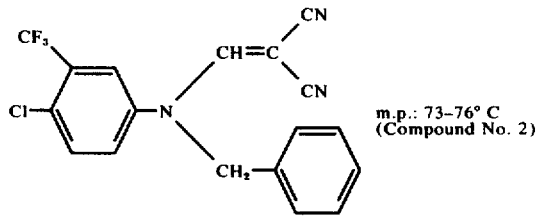

m.p.: 73–76° C
(Compound No. 2)

EXAMPLE 2

A. Insecticidal stomach poison action

Cotton plants and potato plants were sprayed with a 0.02% emulsion of the active ingredient (obtained from a 10% emulsifiable concentrate).

After drying of the coating, Spodoptera littoralis or Heliothis virescens larvae in the L-3 stage were placed onto the cotton plants, and Colorada beetle larvae (Leptinotarsa decemlineata) in the L-3 stage onto the potato plants. The test was carried out at 24° C with 60% relative humidity, and the percentage evaluation of the resulting destruction of the larvae was made after 3 days.

Results:

| Compound No. | Destruction after 3 days % | | |
|---|---|---|---|
| | Leptinotarsa decemlineata | Spodoptera littoralis | Heliothis virescens |
| 1 | 100% | 100% | 100% |
| 2 | 90% | 100% | 90% |

B. Persistent insecticidal stomach poison action

The previous test (Spodoptera littoralis and Heliothis virescens) was repeated using a 0.05% instead of a 0.02% emulsion of the active ingredient. The test larvae were placed onto the plants 8 days after the treatment with the respective emulsion of active ingredient and an evaluation of the attained destruction of larvae was made 3 days after infestation.

Results:

| Compound No. | Destruction (%) | |
|---|---|---|
| | Spodoptera littoralis | Heliothis virescens |
| 1 | 100% | 100% |
| 2 | 100% | 100% |

EXAMPLE 3

Action against Chilo suppressalis

Rice seedlings of the species Caloro were planted, 6 plants per pot, in plastic pots so that the root system of the plants became interwoven into the form of a disk. The roots were immersed in a 0.08% solution of active ingredient and then allowed to drain. Five test larvae (Chilo suppressalis larvae in the $L_3$-stage) were placed into each of the required pots and the treated plants were subsequently planted on top of the introduced larvae.

A percentage evaluation of the resulting destruction of the larvae was made after 5 days.

The following were used as comparative substances:

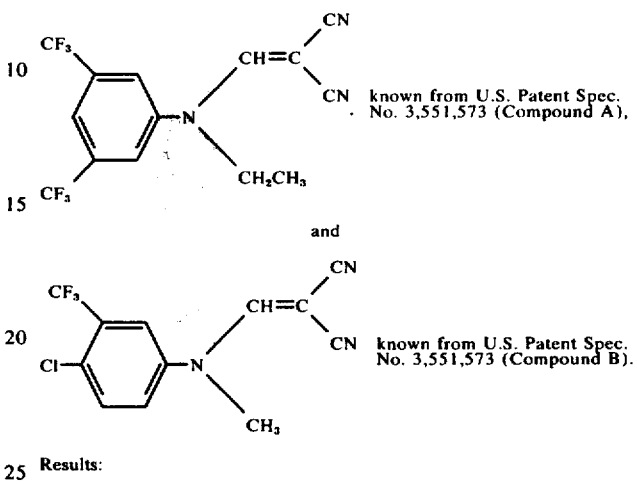

known from U.S. Patent Spec. No. 3,551,573 (Compound A), and known from U.S. Patent Spec. No. 3,551,573 (Compound B).

Results:

| Compound | 1 | 2 | A | B |
|---|---|---|---|---|
| % destruction | 100% | 100% | 0% | 0% |

I claim:
1. A compound of the formula

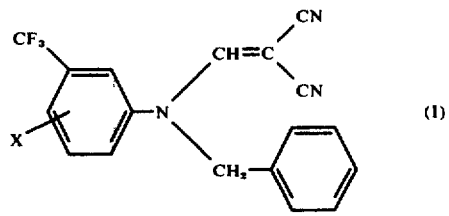

(I)

wherein X represents a chlorine atom or trifluoromethyl group in the 4- or 5-position.

2. N-(2,2-Dicyano-vinyl)-4-benzyl-3,5-bistrifluoromethylaniline according to claim 1.

3. N-(2,2-Dicyano-vinyl)-N-benzyl-3-trifluoromethyl-4-chloroaniline according to claim 1.

4. A solid pesticidal composition which comprises a pesticidally effective amount of a compound as claimed in claim 1, a solid or liquid diluent or carrier and optionally a surface active agent.

5. A method of combatting pests of the class Insecta or of the order Acarina at a locus, which method comprises applying to the locus a compound as claimed in claim 1.

6. A method according to claim 5 herein the locus comprises agricultural or horticultural crops or plants.

7. A method according to claim 6 wherein the locus comprises cotton or rice crops.

* * * * *